United States Patent
Barroyer et al.

(10) Patent No.: US 11,861,764 B2
(45) Date of Patent: Jan. 2, 2024

(54) 3D DEPTH RECONSTRUCTION OF VESSELS IN 2D MEDICAL IMAGES

(71) Applicant: Siemens Healthcare GmbH, Erlangen (DE)

(72) Inventors: Thibaut Barroyer, Monmouth Junction, NJ (US); Mehmet Akif Gulsun, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 519 days.

(21) Appl. No.: 15/734,637

(22) PCT Filed: Jun. 13, 2019

(86) PCT No.: PCT/EP2019/065428
§ 371 (c)(1),
(2) Date: Dec. 3, 2020

(87) PCT Pub. No.: WO2020/030331
PCT Pub. Date: Feb. 13, 2020

(65) Prior Publication Data
US 2021/0158580 A1    May 27, 2021

Related U.S. Application Data

(60) Provisional application No. 62/715,579, filed on Aug. 7, 2018.

(51) Int. Cl.
*G06T 7/00* (2017.01)
*A61B 6/00* (2006.01)
(Continued)

(52) U.S. Cl.
CPC ............ *G06T 11/005* (2013.01); *A61B 6/504* (2013.01); *G06N 3/045* (2023.01); *G06N 3/08* (2013.01);
(Continued)

(58) Field of Classification Search
CPC ................ G06T 11/005; G06T 7/0012; G06T 2207/20084; G06T 2207/30101;
(Continued)

(56) References Cited

U.S. PATENT DOCUMENTS 9,129,417 B2 * 9/2015 Zheng ....................... G06T 7/66
2017/0112372 A1 * 4/2017 Chakravorty ........ A61B 3/1241
(Continued)

FOREIGN PATENT DOCUMENTS

WO    WO2013149863 A1    10/2013
WO    WO2018051336 A1    3/2018

OTHER PUBLICATIONS

Gulsun et al., "Coronary Centerline Extraction via Optimal Flow Paths and CNN Path Pruning", 2016, MICCAI.
(Continued)

*Primary Examiner* — Siamak Harandi

(57) ABSTRACT

Systems and methods are provided for three dimensional depth reconstruction of vessels in two dimensional medical images. A medical image comprising braches of one or more vessels is received. A branch overlap image channel that represents a pixelwise probability that the branches overlap is generated. A set of branch orientation image channels are generated. Each branch orientation image channel is associated with one of a plurality of orientations. Each branch orientation image channel representing a image channel represents a pixelwise probability that the branches are oriented in its associated orientation. A multi-channel depth image is generated based on the branch overlap image channel and the set of branch orientation image channels. Each channel of the multi-channel depth image comprises portions of the branches corresponding to a respective depth.

20 Claims, 5 Drawing Sheets

(51) Int. Cl.
  *G16H 30/40* (2018.01)
  *G06T 11/00* (2006.01)
  *G16H 50/20* (2018.01)
  *G06N 3/08* (2023.01)
  *G06N 3/045* (2023.01)
  *A61B 5/055* (2006.01)
  *A61B 8/08* (2006.01)

(52) U.S. Cl.
  CPC .......... *G06T 7/0012* (2013.01); *G16H 30/40* (2018.01); *G16H 50/20* (2018.01); *A61B 5/055* (2013.01); *A61B 8/0891* (2013.01); *G06T 2207/20084* (2013.01); *G06T 2207/30101* (2013.01)

(58) Field of Classification Search
  CPC . G06T 2207/10116; G06T 7/50; G16H 50/20; G16H 30/40; G06N 3/045; G06N 3/08; A61B 6/504; A61B 5/055; A61B 8/0891
  See application file for complete search history.

(56) References Cited

U.S. PATENT DOCUMENTS

2017/0188993 A1* 7/2017 Hamilton ............. A61B 8/5223
2017/0258433 A1* 9/2017 Gulsun ................ A61B 6/5217
2017/0262981 A1 9/2017 Gulsun et al.
2019/0019347 A1* 1/2019 Auvray .................... G06T 7/75

OTHER PUBLICATIONS

Joshi Vinayak S et al:"Automated method for the identification and analysis of vascular tree structures in retinal vessel network"; Medical Imaging 2011: Computer-Aided Diagnosis, Spie, 1000 20th St. Bellingham WA 98225-6705 USA; vol. 7963, No. 1,; Mar. 3, 2011 (Mar. 3, 2011), pp. 1-11.

International Search Report dated Sep. 18, 2019 in corresponding International Patent Application No. PCT/EP2019/065428.

* cited by examiner

3D DEPTH RECONSTRUCTION OF VESSELS IN 2D MEDICAL IMAGES

CROSS-REFERENCE TO RELATED APPLICATIONS

This application is a national phase filing under 35 U.S.C. § 371 of International Patent Application No. PCT/EP2019/065428, filed Jun. 13, 2019, the disclosure of which is incorporated herein by reference in its entirety.

This application claims the benefit of U.S. Provisional Application No. 62/715,579, filed Aug. 7, 2018, the disclosure of which is herein incorporated by reference in its entirety.

BACKGROUND

The present invention relates generally to three-dimensional (3D) depth reconstruction of vessels in two-dimensional (2D) medical images, and more particularly to machine learning based 3D depth reconstruction of vessels in 2D angiographic images.

BACKGROUND

Detection of blood vessels in medical images facilitates the diagnosis, treatment, and monitoring of many vascular diseases. An important step in vessel detection is centerline tracing to extract a centerline representation of the vessels for enabling specific visualizations or quantitative assessments of the vessels. One conventional method for centerline tracing computes centerline paths by minimizing a cost such as medialness or vesselness. Another conventional method for centerline tracing uses flow based tracing based on estimated orientation tensors. However, such conventional methods for centerline tracing are not able to distinguish between bifurcated vessels and overlapping vessels in two-dimensional medical images.

BRIEF SUMMARY OF THE INVENTION

In accordance with one or more embodiments, systems and methods are provided for three dimensional depth reconstruction of vessels in two dimensional medical images. A medical image comprising branches of one or more vessels is received. A branch overlap image channel that represents a pixelwise probability that the branches overlap is generated. A set of branch orientation image channels are generated. Each branch orientation image channel is associated with one of a plurality of orientations. Each branch orientation image channel represents a pixelwise probability that the branches are oriented in its associated orientation. A multi-channel depth image is generated based on the branch overlap image channel and the set of branch orientation image channels. Each channel of the multi-channel depth image comprises portions of the branches corresponding to a respective depth.

In accordance with one embodiment, the branch overlap image channel is generated using a first trained machine learning network (e.g., an image to image network), the set of branch orientation image channels is generated using a second trained machine learning network (e.g., a fully convolutional neural network), and the multi-channel depth image is generated using a third trained machine learning network (e.g., another image to image network).

In accordance with one embodiment, the set of branch orientation image channels is generated by extracting a plurality of patches from the medical image. For each particular patch of the plurality of patches, a trained fully convolutional neural network is applied to the particular patch to determine a probability, for each respective orientation of the plurality of orientations, that a pixel associated with the particular patch depicts the branches in the respective orientation. For each respective orientation, the probability for each pixel associated with each particular patch for the respective orientation are combined to generate the set of branch orientation image channels.

In accordance with one embodiment, the multi-channel depth image is generated based on pixel intensity values of the medical image.

In accordance with one embodiment, pixels in the branch overlap image channel are highlighted based on the pixelwise probability that the branches overlap and pixels in the set of branch orientation image channels are highlighted based on the pixelwise probability that the branches are oriented in the respective orientation.

In accordance with one embodiment, the multi-channel depth image is generated based on coded high level features previously generated from another branch overlap image channel and another set of branch orientation image channels using a long short-term memory network, where the other branch overlap image channel and the other set of branch orientation image channels are generated from another medical image.

These and other advantages of the invention will be apparent to those of ordinary skill in the art by reference to the following detailed description and the accompanying drawings.

DETAILED DESCRIPTION

The present invention generally relates to methods and systems for three-dimensional (3D) depth reconstruction of vessels in two-dimensional (2D) medical images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while embodiments discussed herein may be discussed with respect to 3D depth reconstruction of vessels in 2D medical images, the present invention is not so limited. The present invention may be applied for 3D depth reconstruction of any tubular object of interest in 2D images of any type.

Figure 1:
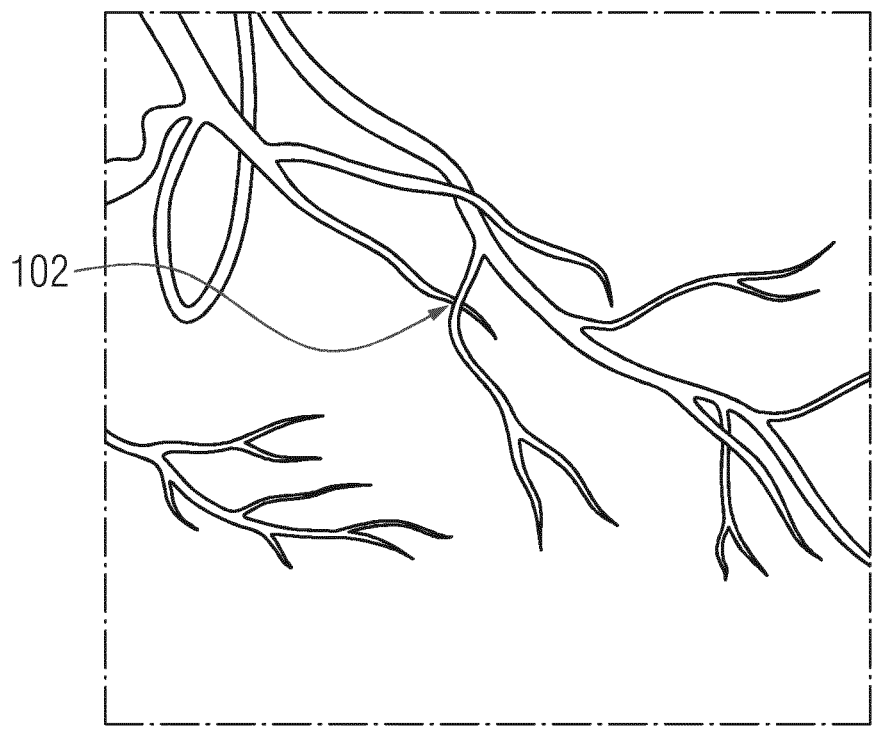
FIG. 1 shows an exemplary two dimensional x-ray medical image depicting branches of blood vessels.

FIG. 1 shows a 2D x-ray medical image 100 of a patient (or any other subject) depicting braches of blood vessels, including a region 102 of overlapping vessels. Medical image 100 may be acquired to facilitate a clinical examination of the patient, such as, e.g., an angiogram. To facilitate vessel detection and other imaging analysis tasks for such clinical examination, centerline tracing techniques may be applied to medical image 100 to extract a centerline representation of the branches of the blood vessels.

Conventional centerline tracing techniques are not able to distinguish between a bifurcation of a branch and an overlapping of branches at region 102. Accordingly, such conventional centerline tracing techniques may incorrectly interpret region 102 as a bifurcation of the branch of the vessel, thereby tracing a false shortcut path of the branch onto the overlapping branches.

Advantageously, embodiments of the present invention apply a series of trained machine learning networks to generate a multi-channel depth image from a 2D medical image, thereby providing a better understanding of the 3D structure of the vessels in the 2D medical image, particularly at regions of overlapping branches, such as, e.g., region 102. The multi-channel depth image may be used for centerline tracing or other imaging analysis tasks with improved results.

Figure 2:
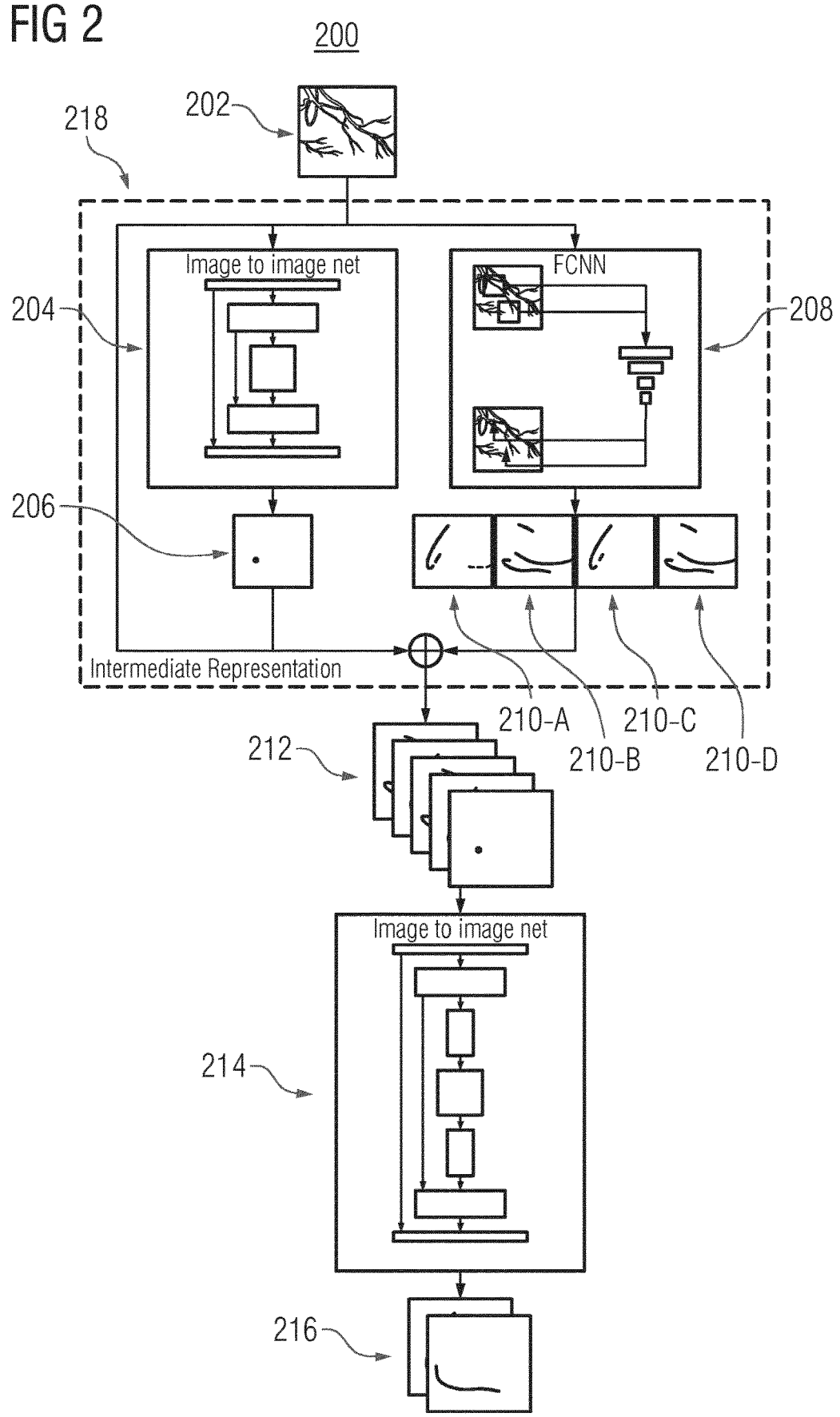
FIG. 2 shows a high level workflow for determining depth information of branches of blood vessels in a two dimensional medical image, in accordance with one or more embodiments.

FIG. 2 shows a high level workflow 200 for determining depth information of branches of blood vessels in a 2D medical image, in accordance with one or more embodiments. Workflow 200 may be performed by any suitable computing device, such as, e.g., computer 502 of FIG. 5.

In workflow 200, a 2D medical image 202 is received. Medical image 202 shows branches of blood vessels, which may include one or more overlapping blood vessels. Medical image 202 is shown in workflow 200 as an x-ray image, however it should be understood that medical image 202 may be any 2D medical image of any suitable modality.

A trained image to image network 204 receives medical image 202 as input for pixelwise prediction of overlapping branches of blood vessels in medical image 202. Image to image network 204 outputs a branch overlap image channel 206 representing a probability mask for overlapping blood vessels, where each pixel in branch overlap image channel 206 is associated with a probability that the pixel depicts overlapping branches. Pixels that have a high probability of overlapping blood vessels are highlighted in branch overlap image channel 206.

A trained fully convolutional neural network (FCNN) 208 receives patches of medical image 202 as input for pixelwise prediction of the orientation of blood vessels. For each patch, FCNN 208 outputs a set of scalars each corresponding to an orientation probability for a respective orientation of a plurality of orientations. The orientation probability for a respective orientation of a patch represents a probability that a pixel (e.g., the center pixel) of the patch depicts a branch oriented in the respective orientation. For each respective orientation, the scalars corresponding to the respective orientation are combined for each pixel in the medical image from which the patches are extracted, thereby forming branch orientation image channels 210-A, 210-B, 210-C, and 210-D (hereinafter referred to branch orientation image channels 210) each for a respective orientation. Each branch orientation image channel 210 for a respective orientation represents a probability mask for the orientation of the blood vessel, where each pixel in the branch orientation image channel is associated with a probability that the pixel depicts a branch oriented in the respective orientation. Pixels in each branch orientation image channel 210 that have a high orientation probability are highlighted. As shown in workflow 200, the set of branch orientation image channels 210 comprises a branch orientation image channel 210-A for a first diagonal orientation (e.g., the diagonal formed between a lower left corner to an upper right corner), a branch orientation image channel 210-B for a horizontal orientation, a branch orientation image channel 210-C for a vertical orientation, and a branch orientation image channel 210-D for a horizontal orientation second diagonal direction (e.g., the diagonal formed between an upper left corner to a lower right corner).

Image to image network 204, branch overlap image channel 206, FCNN 208, and set of branch orientation image channels 210 are represented as intermediate representation 218 for simplicity, e.g., in describing FIG. 4 below.

Branch overlap image channel 206 and set of branch orientation image channels 210 are concatenated to form concatenated image channels 212. It should be understood that concatenated image channels 212 may additionally or alternatively include other image channels. For example, as shown in FIG. 2, branch overlap image channel 206 and set of branch orientation image channels 210 may also be concatenated with medical image 202, representing pixelwise intensity values, to form concatenated image channels 212. In another example, branch overlap image channel 206 and set of branch orientation image channels 210 may be concatenated with a vesselness image channel representing a pixelwise probability that a pixel represents a vessel to form concatenated image channels 212. Other types of image channels are also contemplated.

A trained image to image network 214 receives concatenated image channels 212 as input for generating a multi-channel depth image 216, where each depth image channel corresponds to a respective depth and highlights pixels of branches associated with (e.g., located at) the respective depth. Advantageously, multilayer depth image 216 may be used for centerline tracing (or other imaging analysis tasks) to distinguish between vessel bifurcations and vessel overlaps to avoid shortcuts.

It should be understood that while networks 204, 208, and 214 are shown in workflow 200 as image to image network 204, FCNN 208, and image to image network 214, respectively, any suitable machine learning network, such as, e.g., a convolutional neural network (CNN) may be employed. For example, image to image networks 204 and 214 may be a FCNN or FCNN 208 may be an image to image network.

Figure 3:
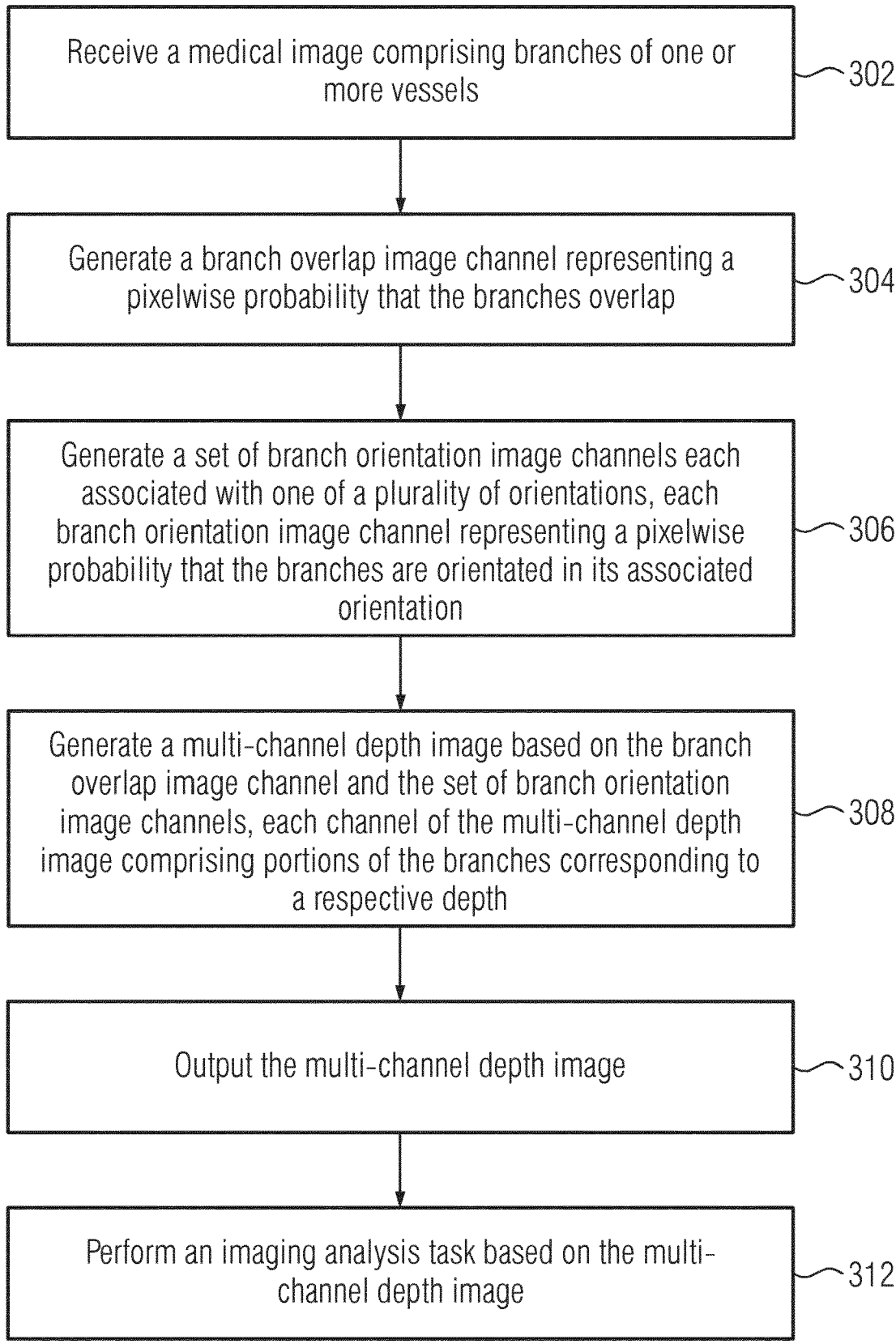
FIG. 3 shows a method for determining depth information of vessels in a two dimensional medical image, in accordance with one or more embodiments.

FIG. 3 shows a method 300 for determining depth information of vessels in a 2D medical image, in accordance with one or more embodiments. Method 300 shows a detailed implementation for performing workflow 200 of FIG. 2, in accordance with one embodiment. Method 300 may be performed by any suitable computing device, such as, e.g., computer 502 of FIG. 5.

At step 302, a medical image is received. The medical image comprises branches of one or more vessels, and may include regions of overlapping branches. In one embodiment, the medical image is an angiogram x-ray image, however it should be understood that the medical image may be of any suitable modality, such as, e.g., magnetic resonance imaging (MRI), computed tomography (CT), ultrasound (US), single-photon emission computed tomography (SPECT), positron emission tomography (PET), etc. The medical image may be received from one or more medical imaging systems or by loading a previously stored medical image acquired using one or more medical imaging systems.

At step 304, a branch overlap image channel is generated representing a pixelwise probability that the branches overlap based on the medical image. The branch overlap image channel represents a probability mask with pixels corresponding to the medical image. Each pixel in the branch overlap image channel is associated with a probability that the pixel depicts overlapping blood vessels.

The branch overlap image channel may be visualized by highlighting pixels based on their associated probability. In one embodiment, pixels in the branch overlap image channel having a high probability of overlapping blood vessels are highlighted. For example, an intensity of a pixel may be determined as being proportional to its associated probability such that a pixel associated with a probability of 0% is determined to have an intensity value of 0 while a pixel associated with a probability of 100% is determined to have an intensity value of 255. In another example, the branch overlap image channel represents a binary probability mask such that a pixel associated with a probability that satisfies a threshold may be highlighted (e.g., by setting its intensity value to 255), while a pixel associated with a probability that does not satisfy the threshold is not highlighted (e.g., by setting its intensity value to 0).

In one embodiment, the branch overlap image channel is generated using a first trained machine learning network. In one embodiment, the first trained machine learning network is a trained image to image network. The trained image to image network is trained during a prior training stage using input/output pairs of training images. The trained image to image network includes an encoding network (or encoder) and a decoding network (or decoder). The encoding network has a series of layers that code or down sample the received medical image into a code whose size is substantially less than the size of the received medical image to thereby extract high level representations or features of the received medical image. The decoding network has a series of layers that will then decode the code to convert the high-level representations back to a pixel-level semantic representation to thereby generate the branch overlap image channel. All the intermediate information generated in the encoding network is shared with the decoding network so that no information is lost in the encoding process. It should be understood that the first trained machine learning network may be any suitable machine learning network, such as, e.g., any other convolutional neural network (e.g., FCNN), and is not limited to an image to image network.

At step 306, a set of branch orientation image channels each associated with a respective orientation of a plurality of orientations are generated based on the medical image. Each branch orientation image channel represents a pixelwise probability that the branches are orientated in the respective orientation. In one embodiment, the plurality of orientations comprise a vertical orientation, a horizontal orientation, a first diagonal orientation (e.g., the diagonal formed between a lower left corner to an upper right corner), and a second diagonal direction (e.g., the diagonal formed between an upper left corner to a lower right corner). Other orientations are also contemplated.

Each branch orientation image channel of the set of branch orientation image channels represents a probability mask with pixels corresponding to the medical image. Each pixel in the branch orientation image channel is associated with a probability that a branch in the pixel is oriented in the respective orientation.

In one embodiment, the set of branch orientation image channels is generated using a second trained machine learning network. In one embodiment, the second trained machine learning network is a trained FCNN. The trained FCNN is trained during a prior training stage using annotated training image patches. The trained FCNN receives a plurality of patches extracted from the medical image as the input and, for each patch, generates a set of scalars (each corresponding to a respective orientation) as the output representing a probability that the patch is oriented in the respective orientation. The FCNN includes an input layer, multiple convolutional layers, and an output layer. The connections between consecutive layers are defined by a set of convolutional kernel weights and biases. The input layer corresponds to image data of the input image (e.g., the extracted patches from the medical image). The output layer corresponds to the set of scalars.

The plurality of patches may be extracted from the medical image using any suitable approach. In one embodiment, a uniform sampling distribution may be used to define evenly spaced sampling points. For example, a patch centered around each pixel in the medical image may be extracted. However, the present invention is not limited thereto and other possible sampling distributions may be used. The patches may be of any suitable size.

For each patch, the FCNN outputs a set of scalars each corresponding to an orientation probability for a respective orientation. The orientation probability for a respective orientation of a patch represents a probability that the center pixel of the patch is oriented in the respective orientation. By applying the FCNN to patches centered around, e.g., each pixel in the medical image, an orientation probability for each respective orientation can be predicted for each pixel in the medical image.

For each respective orientation, the scalars corresponding to the respective orientation are combined for each pixel in the medical image from which the patches are extracted, thereby forming the branch orientation image channel for each respective orientation.

Pixels in each of the branch orientation image channels may be highlighted based on their associated probability. In one embodiment, pixels in the branch orientation image channel having a high probability of overlapping blood vessels are highlighted. For example, the pixels in the branch orientation image channel may be highlighted as discussed above with respect to the branch overlap image channel in step 304.

It should be understood that the second trained machine learning network may be any suitable machine learning network, such as, e.g., any other convolutional neural network (e.g., an image to image network), and is not limited to a FCNN.

At step 308, a multi-channel depth image is generated based on the branch overlap image channel and the set of branch orientation image channels. Each depth image channel of the multi-channel depth image comprises portions of the branches corresponding to a respective depth.

In one embodiment, the multi-channel depth image is generated using a third trained machine learning network. In one embodiment, the third trained machine learning network is a trained image to image network. The trained image to image network is trained during a prior training stage using input/output pairs of training images. The branch overlap image channel and the set of branch orientation image channels are concatenated and the concatenated image channels are input into the trained image to image network. The trained image to image network outputs a plurality of depth image channels, each corresponding to a respective depth, forming the multi-channel depth image. Each depth image channel represents a probability mask with pixels corresponding to the medical image. Each pixel in the depth image channel is associated with a probability that the pixel depicts branches located at the respective depth.

The depth image channels may be visualized by highlighting pixels based on their associated probability. In one embodiment, pixels in the depth image channel having a high probability of overlapping blood vessels are highlighted. For example, the pixels in the depth image channel may be highlighted as discussed above with respect to the branch overlap image channel in step 304.

It should be understood that while the multi-channel depth image is described herein as being generated based on concatenated image channels comprising the branch overlap image channel and the set of branch orientation image channels at step 308, the concatenated image channels may additionally or alternatively comprise any suitable image channel. In one example, the concatenated image channels may include the medical image received at step 302, representing pixelwise intensity values. In another example, the concatenated image channels may include a vesselness image channel representing a pixelwise probability that a pixel represents a vessel.

It should be understood that the third trained machine learning network may be any suitable machine learning network, such as, e.g., any other convolutional neural network (e.g., a FCNN), and is not limited to an image to image network.

At step 310, the multi-channel depth image is output. The multi-channel depth image can be output by displaying the multi-channel depth image on a display device of a computer system, storing the multi-channel depth image on a memory or storage of a computer system, or by transmitting the multi-channel depth image to a remote computer system, e.g., for further processing.

At step 312, an imaging analysis task is performed based on the multi-channel depth image. In one embodiment, the imaging analysis task is centerline tracing of the branches of the vessels in the medical image. Other imaging analysis tasks are also contemplated.

In accordance with one embodiment, workflow 200 of FIG. 2 can be modified to leverage high level features previously coded by the encoding network of image to image network 214 during one or more prior analyses of medical images temporally acquired over a period of time. In particular, image to image network 214 of FIG. 2 can be implemented with a long short-term memory (LSTM) network, which provides long term memory controlled by opening or closing an input gate, an output gate, and/or a forget gate. Advantageously, image to image network 214 implemented with an LSTM network enables high level features encoded by the encoding network (of image to image network 214) to be stored and subsequently used by the decoding network (of image to image network 214) to generate more accurate multi-channel depth images.

Figure 4:
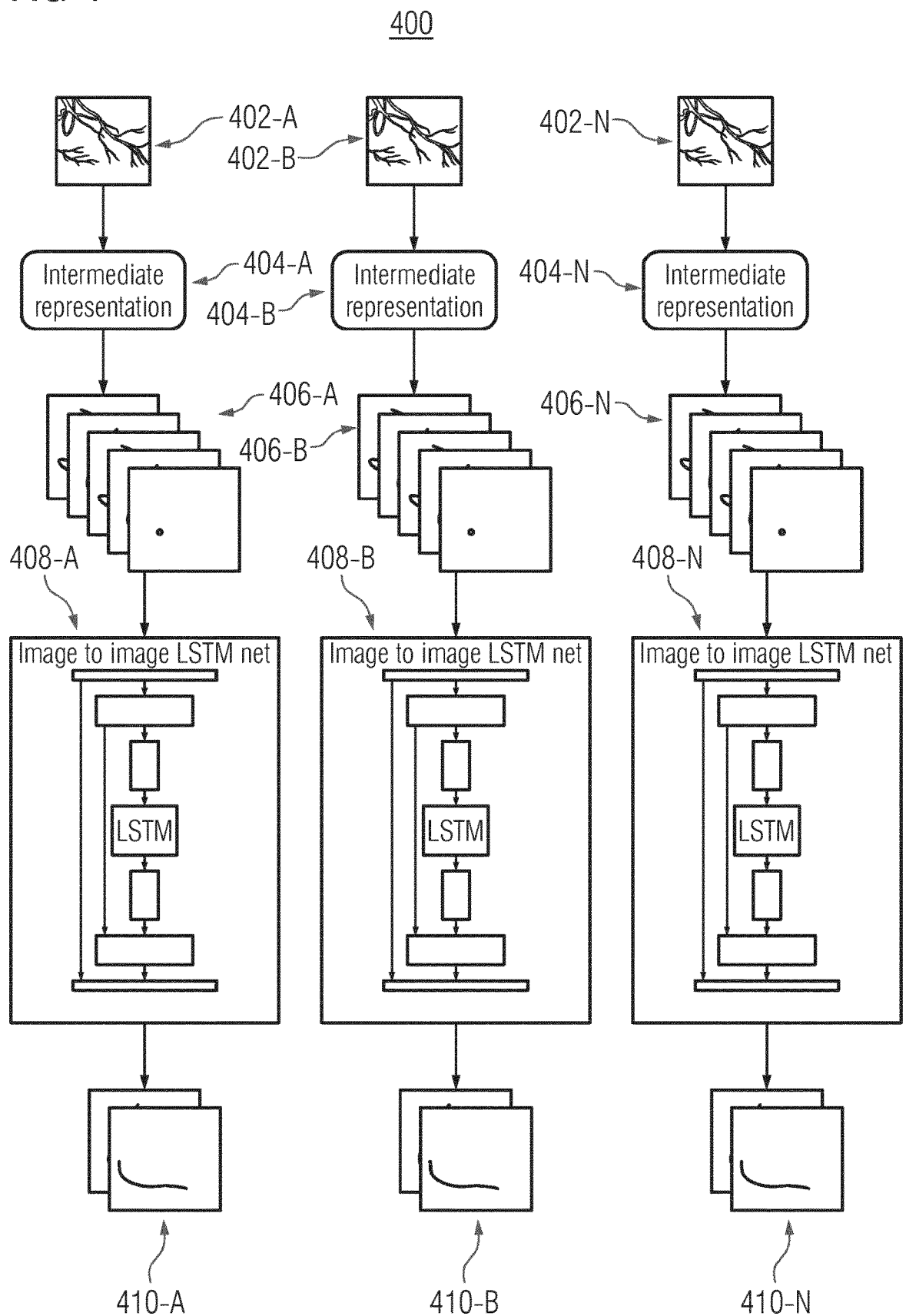
FIG. 4 shows a high level workflow for determining depth information of branches of vessels in two dimensional medical images by leveraging high level features previously coded during prior analyses of medical images, in accordance with one or more embodiments.

FIG. 4 shows a high level workflow 400 for determining depth information of branches of vessels in 2D medical images by leveraging high level features previously coded during prior analyses of medical images temporally acquired over a period of time, in accordance with one or more embodiments. In workflow 400, intermediate representations 404-A, 404-B, . . . , 404-N (collectively referred to as intermediate representations 404) represent intermediate representation 218 shown in FIG. 2. While intermediate representations 404-A, 404-B, . . . , 404-N and image to image long short-term memory (LSTM) networks 408-A, 408-B, . . . , 408-N (collectively referred to as image to image LSTM networks 408) are functionally shown as separate instances in workflow 400 for ease of understanding to show temporal analysis of medical images 402, it should be understood that the same intermediate representation 404 and the same image to image LSTM network 408 is applied for each of the medical images 402 (i.e., the same image to image network and FCNN with the same learned weights are used for each instance of intermediate representation 404 and the same image to image LSTM network with the same learned weights are used for each instance of image to image LSTM network 408 shown in workflow 400).

Similar to workflow 200 of FIG. 2, in workflow 400, 2D medical images 402-A, 402-B, . . . , 402-N (collectively referred to as medical images 402) are received, where N is any integer. Medical images 402 comprise branches of blood vessels, which may include overlapping branches. Medical images 402 may be of any suitable modality temporally acquired over a period of time. Medical images 402 are input into a respective intermediate representation 404 to generate respective concatenated image channels 406-A, 406-B, . . . , 406-N (collectively referred to as concatenated image channels 406). Each of the concatenated image channels 406 include a branch overlap image channel and a set of branch orientation image channels. In some embodiments, concatenated image channels 406 may also include the respective medical image 402 representing pixelwise intensity values Workflow 400 modifies workflow 200 of FIG. 2 by replacing image to image network 214 with image to image LSTM network 408. Accordingly, concatenated image channels 406 are input into trained image to image LSTM network 408 to generate respective multi-channel depth images 410-A, 410-B, . . . , 410-N (collectively referred to as multi-channel depth images 410). Image to image LSTM network 408 comprise an image to image network implemented with an LSTM network. The LSTM network enables the image to image network to store and subsequently use high level features previously coded by the encoding network during prior analyses to generate more accurate multi-channel depth images 410, as represented by the connection between image to image LSTM network 408-A, 408-B, . . . , 408-N.

Accordingly, image to image LSTM network 408 receives respective concatenated image channels 406. The encoding network of the image to image LSTM networks 408 codes the received concatenated image channels 406 to a code representing high level representations or features of the received concatenated image channels 406. The code is stored by the LSTM network for subsequent use by the decoding network of the image to image LSTM networks 408. As such, the decoding network of the image to image LSTM networks 408 decodes the code generated by the encoding network from that respective concatenated image channel 406 and one or more codes stored by the LSTM network previously generated by the encoding network (if available).

It should be understood that image to image LSTM network 408 may use any previously coded high level features generated by the encoding network and is not limited to the immediately prior coded high level features generated by the encoding network. For example, image to image LSTM network 408-N may use the previously coded high level features from the instance of image to image LSTM network 408-A and/or the instance of LSTM network 408-B to generate multi-channel depth image 410-N.

It should be understood that while the exemplary embodiment of workflow 400 is shown using an image to image network implemented with an LSTM network, the present invention is not so limited. Any type of CNN (e.g., FCNN) implemented with any type of recurrent neural network (RNN) architecture, such as, e.g., a gated recurrent unit (GRU).

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-4. Certain steps or functions of the methods and workflows described herein, including one or more of the steps or functions of FIGS. 2-4, may be performed by a server or by another processor in a network-based cloud-computing system. Certain steps or functions of the methods and workflows described herein, including one or more of the steps of FIGS. 2-4, may be performed by a client computer in a network-based cloud computing system. The steps or functions of the methods and workflows described herein, including one or more of the steps of FIGS. 2-4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
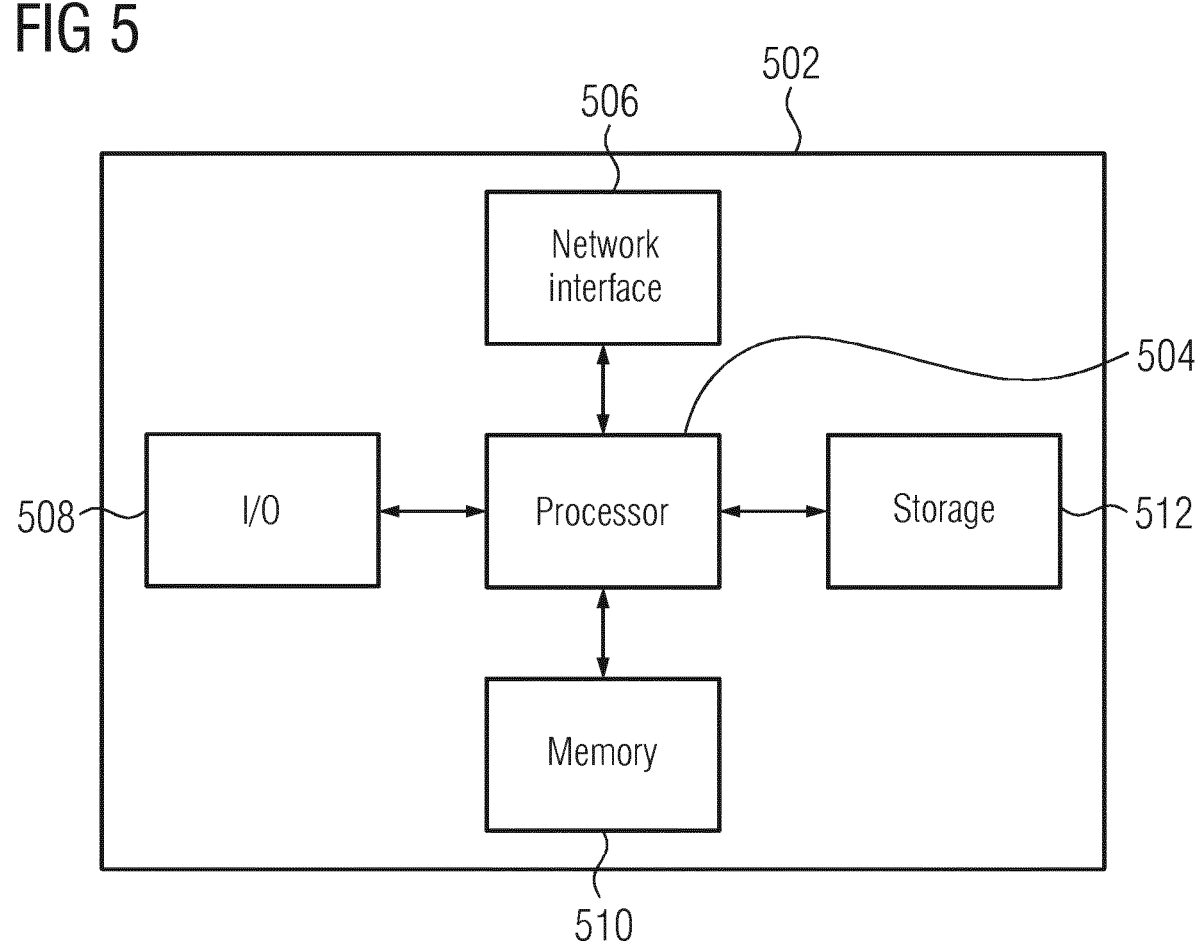
FIG. 5 shows a high-level block diagram of a computer.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIGS. 2-4 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIGS. 2-4. Accordingly, by executing the computer program instructions, the processor 504 executes the method and workflow steps or functions of FIGS. 2-4. Computer 504 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

Any or all of the systems and apparatus discussed herein may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
receiving a medical image comprising branches of one or more vessels;
generating a branch overlap image channel representing a pixelwise probability that the branches overlap;
generating a set of branch orientation image channels each associated with one of a plurality of orientations, each branch orientation image channel representing a pixelwise probability that the branches are oriented in its associated orientation; and
generating a multi-channel depth image based on the branch overlap image channel and the set of branch orientation image channels, each channel of the multi-channel depth image comprising portions of the branches corresponding to a respective depth.

2. The method of claim 1, wherein:
generating a branch overlap image channel representing a pixelwise probability that the branches overlap comprises generating the branch overlap image channel using a first trained machine learning network;
generating a set of branch orientation image channels each associated with one of a plurality of orientations comprises generating the set of branch orientation image channels using a second trained machine learning network; and
generating a multi-channel depth image based on the branch overlap image channel and the set of branch orientation image channels comprises generating the multi-channel depth image using a third trained machine learning network.

3. The method of claim 2, wherein the first trained machine learning network comprises a trained image to image network, the second trained machine learning network comprises a trained fully convolutional neural network, and the third trained machine learning network comprises another trained image to image network.

4. The method of claim 1, wherein the plurality of orientations comprises a vertical orientation, a horizontal orientation, a first diagonal orientation, and a second diagonal orientation.

5. The method of claim 1, wherein generating a set of branch orientation image channels each associated with one of a plurality of orientations comprises:
extracting a plurality of patches from the medical image;
for each particular patch of the plurality of patches:
applying a trained fully convolutional neural network to the particular patch to determine a probability, for each respective orientation of the plurality of orientations, that a pixel associated with the particular patch depicts the branches in the respective orientation; and
for each respective orientation, combining the probability for each pixel associated with each particular patch for the respective orientation to generate the set of branch orientation image channels.

6. The method of claim 1, further comprising:
highlighting pixels in the branch overlap image channel based on the pixelwise probability that the branches overlap; and
highlighting pixels in the set of branch orientation image channels based on the pixelwise probability that the branches are oriented in their associated orientation.

7. The method of claim 1, wherein generating a multi-channel depth image based on the branch overlap image channel and the set of branch orientation image channels comprises:
generating the multi-channel depth image based on coded high level features previously generated from another branch overlap image channel and another set of branch orientation image channels, the other branch overlap image channel and the other set of branch orientation image channels being generated from another medical image.

8. The method of claim 7, wherein generating the multi-channel depth image based on coded high level features previously generated from another branch overlap image channel and another set of branch orientation image channels comprises:
generating the multi-channel depth image using a long short-term memory network.

9. The method of claim 1, wherein generating a multi-channel depth image based on the branch overlap image channel and the set of branch orientation image channels comprises:
generating the multi-channel depth image based on pixel intensity values of the medical image.

10. The method of claim 1, further comprising:
performing an imaging analysis task based on the multi-channel depth image.

11. An apparatus comprising:
means for receiving a medical image comprising branches of one or more vessels;
means for generating a branch overlap image channel representing a pixelwise probability that the branches overlap;
means for generating a set of branch orientation image channels each associated with one of a plurality of orientations, each branch orientation image channel representing a pixelwise probability that the branches are oriented in its associated orientation; and
means for generating a multi-channel depth image based on the branch overlap image channel and the set of branch orientation image channels, each channel of the multi-channel depth image comprising portions of the branches corresponding to a respective depth.

12. The apparatus of claim 11, wherein:
the means for generating a branch overlap image channel representing a pixelwise probability that the branches overlap comprises means for generating the branch overlap image channel using a trained image to image network;

the means for generating a set of branch orientation image channels each associated with one of a plurality of orientations comprises means for generating the set of branch orientation image channels using a trained fully convolutional neural network; and the means for generating a multi-channel depth image based on the branch overlap image channel and the set of branch orientation image channels comprises means for generating the multi-channel depth image using another trained image to image network.

13. The apparatus of claim 11, wherein the plurality of orientations comprises a vertical orientation, a horizontal orientation, a first diagonal orientation, and a second diagonal orientation.

14. The apparatus of claim 11, wherein the means for generating a set of branch orientation image channels each associated with one of a plurality of orientations comprises:

means for extracting a plurality of patches from the medical image;

for each particular patch of the plurality of patches:

means for applying a trained fully convolutional neural network to the particular patch to determine a probability, for each respective orientation of the plurality of orientations, that a pixel associated with the particular patch depicts the branches in the respective orientation; and for each respective orientation, means for combining the probability for each pixel associated with each particular patch for the respective orientation to generate the set of branch orientation image channels.

15. A non-transitory computer readable medium storing computer program instructions, the computer program instructions when executed by a processor cause the processor to perform operations comprising:

receiving a medical image comprising branches of one or more vessels;

generating a branch overlap image channel representing a pixelwise probability that the branches overlap;

generating a set of branch orientation image channels each associated with one of a plurality of orientations, each branch orientation image channel representing a pixelwise probability that the branches are oriented in its associated orientation; and generating a multi-channel depth image based on the branch overlap image channel and the set of branch orientation image channels, each channel of the multi-channel depth image comprising portions of the branches corresponding to a respective depth.

16. The non-transitory computer readable medium of claim 15, wherein:

generating a branch overlap image channel representing a pixelwise probability that the branches overlap comprises generating the branch overlap image channel using a first trained machine learning network;

generating a set of branch orientation image channels each associated with one of a plurality of orientations comprises generating the set of branch orientation image channels using a second trained machine learning network; and generating a multi-channel depth image based on the branch overlap image channel and the set of branch orientation image channels comprises generating the multi-channel depth image using a third trained machine learning network.

17. The non-transitory computer readable medium of claim 15, the operations further comprising:

highlighting pixels in the branch overlap image channel based on the pixelwise probability that the branches overlap based on the medical image; and highlighting pixels in the set of branch orientation image channels based on the pixelwise probability that the branches are oriented in their associated orientation.

18. The non-transitory computer readable medium of claim 15, wherein generating a multi-channel depth image based on the branch overlap image channel and the set of branch orientation image channels comprises:

generating the multi-channel depth image based on coded high level features previously generated from another branch overlap image channel and another set of branch orientation image channels, the other branch overlap image channel and the other set of branch orientation image channels being generated from another medical image.

19. The non-transitory computer readable medium of claim 18, wherein generating the multi-channel depth image based on coded high level features previously generated from another branch overlap image channel and another set of branch orientation image channels comprises:

generating the multi-channel depth image using a long short-term memory network.

20. The non-transitory computer readable medium of claim 15, wherein generating a multi-channel depth image based on the branch overlap image channel and the set of branch orientation image channels comprises:

generating the multi-channel depth image based on pixel intensity values of the medical image.

* * * * *